(12) United States Patent
Holman et al.

(10) Patent No.: US 7,691,137 B2
(45) Date of Patent: Apr. 6, 2010

(54) ROTATABLE SHEATH, ASSEMBLY AND METHOD OF MANUFACTURE OF SAME

(75) Inventors: Thomas J. Holman, Minneapolis, MN (US); Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 220 days.

(21) Appl. No.: 10/952,007

(22) Filed: Sep. 28, 2004

(65) Prior Publication Data

US 2006/0074476 A1 Apr. 6, 2006

(51) Int. Cl.
*A61F 2/84* (2006.01)
(52) U.S. Cl. ...................................... 623/1.11
(58) Field of Classification Search ............. 606/194, 606/200, 108; 623/1.11–1.12, 1.35, 1.23; 604/96.01, 103.03–103.05, 171
See application file for complete search history.

(56) References Cited

U.S. PATENT DOCUMENTS

| | | | |
|---|---|---|---|
| 5,116,318 A * | 5/1992 | Hillstead | 604/103.14 |
| 5,257,974 A * | 11/1993 | Cox | 604/103.05 |
| 5,484,418 A | 1/1996 | Quiachon et al. | 604/167 |
| 5,507,769 A | 4/1996 | Marin et al. | 606/198 |
| 5,527,325 A | 6/1996 | Conley et al. | 606/159 |
| 5,609,627 A | 3/1997 | Goicoechea et al. | 623/1 |
| 5,683,450 A | 11/1997 | Goicoechea et al. | 623/1 |
| 5,693,086 A | 12/1997 | Goicoechea et al. | 623/1 |
| 5,749,825 A * | 5/1998 | Fischell et al. | 600/3 |
| 5,843,027 A * | 12/1998 | Stone et al. | 604/509 |
| 5,843,119 A | 12/1998 | Shmulewitz | 606/198 |
| 5,916,263 A | 6/1999 | Goicoechea et al. | 623/1 |
| 5,938,696 A | 8/1999 | Goicoechea et al. | 623/1 |
| 5,993,484 A | 11/1999 | Shmulewitz | 623/1 |
| 6,210,431 B1 | 4/2001 | Power | 623/1.11 |
| 6,302,906 B1 | 10/2001 | Goicoechea et al. | 623/1.11 |

(Continued)

FOREIGN PATENT DOCUMENTS

EP 0 669 142 8/1995

(Continued)

OTHER PUBLICATIONS

U.S. Appl. No. 10/657,472, filed Sep. 8, 2003, Eidenschink.

(Continued)

*Primary Examiner*—Todd E Manahan
*Assistant Examiner*—Ryan J Severson
(74) *Attorney, Agent, or Firm*—Crompton, Seager & Tufte, LLC

(57) ABSTRACT

A medical device comprises a catheter having a catheter shaft and a medical balloon positioned thereon, as well as a rotatable assembly disposed about the balloon. The balloon has a pre-expansion state and an expanded state. The rotatable assembly comprises a sheath, wherein the sheath is disposed about the balloon in both the pre-expansion state and in the expanded state. The sheath is rotatable about the balloon in the pre-expansion state. The sheath comprises an inner layer and an outer layer, the inner layer is in rotatable contact with the balloon and the outer layer is disposed about the inner layer. The inner layer is at least partially constructed of at least one material having a durometer value greater than that of the outer layer.

23 Claims, 8 Drawing Sheets

U.S. PATENT DOCUMENTS

| | | | | |
|---|---|---|---|---|
| 6,383,213 | B2 | 5/2002 | Wilson et al. | 623/1.11 |
| 6,387,120 | B2 | 5/2002 | Wilson et al. | 623/1.11 |
| 6,533,806 | B1 * | 3/2003 | Sullivan et al. | 623/1.11 |
| 6,596,020 | B2 * | 7/2003 | Vardi et al. | 623/1.11 |
| 6,660,030 | B2 | 12/2003 | Shaolian et al. | 623/1.11 |
| 6,682,536 | B2 | 1/2004 | Vardi et al. | 606/108 |
| 2002/0052640 | A1 * | 5/2002 | Bigus et al. | 623/1.11 |
| 2004/0097881 | A1 | 5/2004 | Brustad et al. | 604/164.07 |

FOREIGN PATENT DOCUMENTS

| | | |
|---|---|---|
| WO | WO 2005/025458 | 3/2005 |
| WO | WO 2005/067818 | 7/2005 |

OTHER PUBLICATIONS

U.S. Appl. No. 10/375,689, filed Feb. 27, 2003, Eidenschink.
U.S. Appl. No. 10/747,546, filed Dec. 29, 2003, Eidenschink et al.
U.S. Appl. No. 10/757,646, filed Jan. 13, 2004, Weber et al.
U.S. Appl. No. 10/784,337, filed Feb. 23, 2004, Eidenschink.
U.S. Appl. No. 10/863,724, filed Jun. 8, 2004, Tran et al.

* cited by examiner

ROTATABLE SHEATH, ASSEMBLY AND METHOD OF MANUFACTURE OF SAME

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Catheter systems such as angioplasty catheters, and stent delivery systems, as well as the stents associated therewith, are widely used in the treatment of stenoses, aneurysms, lesions, and other abnormalities within blood vessels and other body lumens. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

Treatment at bifurcation sites has been difficult. Although efforts have been made to use a stent at bifurcations, these sites have previously been problematic to treat. The specialty stents designed for bifurcations generally need specific alignment, radially as well as longitudinally. For example, U.S. Pat. No. 5,749,825 is representative of a catheter system that is intended to treat stenoses at an arterial bifurcation. The disclosure of U.S. Pat. No. 5,749,825 is hereby incorporated by reference.

Often stent delivery systems are employed to deliver multiple stents to the primary and/or secondary vessels surrounding a vessel bifurcation. One or more catheters may be required to deploy each stent. Stents deployed by such systems generally have an opening or branch which allows for unimpeded blood flow into a side branch artery, and through which one or more branch stents may be subsequently delivered. However, problems are still encountered in orienting such stents relative to the branch openings at the bifurcation of the primary and secondary passages. Moreover, such bifurcated assemblies are typically specially manufactured at an increased cost over a more standard stent intended for single vessel deployment.

In delivering one or more stents to a vessel bifurcation, many devices have relied on the application of torque to the catheter shaft from outside of the patient to orient one or more medical devices within the vessel passage. The use of such active application of torque on a catheter within a vessel has several possible consequences including potential strain inadvertently applied to the contacted vessel, as well as control and precision issues. To avoid the need of having to actively apply torque to the catheter shaft, in order to orient the and/or stent, catheter assemblies have been developed which are equipped with a rotatable sheath, that is capable of rotating about the catheter shaft and/or balloon. A stent may be initially mounted to the sheath and a secondary guidewire engaged to the sheath directs the orientation of the sheath as the assembly is advanced through a body lumen. Some examples of such catheter assemblies have been shown and described in the following publications:

U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; U.S. patent application Ser. No. 10/757,646, filed Jan. 13, 2004 and entitled Bifurcated Stent Delivery System; and U.S. patent application Ser. No. 10/784,337, filed Feb. 23, 2004 and entitled Apparatus and Method for Crimping a Stent Assembly; the entire content of each of which are incorporated herein by reference.

Upon a review of the above referenced publications it will be recognized that contact between the sheath and the balloon, and/or the catheter shaft, will affect the capability of the sheath to readily and freely rotate. Desirably the frictional interface between the sheath and balloon, and/or catheter shaft, should be minimized to encourage the free rotation of the sheath. In addition, it would be further desirable to provide such rotatable sheaths with one or more configurations that may provide a more directed or controlled delivery of the stent during balloon expansion.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

As used herein the term 'stent' refers to an expandable prosthesis for implantation into a body lumen or vessel and includes devices such as stents, grafts, stent-grafts, vena cava filters, etc. In some embodiments a stent may be at least partially constructed of any of a variety of materials such as stainless steel, nickel, titanium, nitinol, platinum, gold, chrome, cobalt, as well as any other metals and their combinations or alloys. A stent may be at least partially constructed of a polymer material. A stent may be at least partially constructed of a shape-memory polymer or material. A stent may be balloon expandable, self-expandable, hybrid expandable or a combination thereof In some embodiments a stent may include one or more areas, bands, coatings, members etc that is (are) detectable by imaging modalities such as X-Ray, MRI or ultrasound. In some embodiments at least a portion of the stent is at least partially radiopaque. In some embodiments a stent may include one or more therapeutic and/or lubricious coatings applied thereto.

Catheter systems for delivery of one or more stents or stent segments, wherein at least one of the stents is mounted on the catheter with a freely rotating deployment sheath and assembly are described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery;

U.S. patent application Ser. No. 10/747,546, filed Dec. 29, 2003 and entitled Rotating Balloon Expandable Sheath Bifurcation Delivery System; U.S. patent application Ser. No. 10/757,646, filed Jan. 13, 2004 and entitled Bifurcated Stent Delivery System; U.S. patent application Ser. No. 10/784,337, filed Feb. 23, 2004 and entitled Apparatus and Method for Crimping a Stent Assembly; and U.S. patent application Ser. No. 10/863,724, filed Jun. 8, 2004 and entitled Bifurcation Stent Delivery Sheath, the entire content of each being incorporated herein by reference.

Some embodiments of the present invention are directed to such catheter systems and rotating assemblies wherein the catheter is a balloon catheter having a balloon and at least one rotatable sheath or sheath section at least partially disposed thereabout.

In at least one embodiment of the invention at least one stent is disposed about the at least one sheath or sheath section prior to delivery. A guidewire is moveably engaged to the rotatable sheath and/or stent in order to allow the rotatable sheath to rotatingly align the stent or stents at a vessel bifurcation. In some embodiments the guidewire extends between the stent and sheath exiting radially from a guidewire hole in the wall of the sheath and/or a secondary opening in the stent.

In at least one embodiment the catheter system employs a guidewire housing through which the guidewire is passed. The guidewire housing is fixedly engaged to and/or through the rotatable sheath and the stent is disposed thereabout. In some embodiments the guidewire housing extends through the secondary opening of the stent whereupon the guidewire exits the guidewire housing. In some embodiments the guidewire extends from a region of the rotatable sheath proximal to the stent to a distal region and/or distal end of the stent.

In at least one embodiment the guidewire housing has a length, of which a majority is engaged to the rotatable sheath. In some embodiments the entire length of the guidewire housing is engaged to the rotatable sheath. The guidewire housing may be integral with the rotatable sheath, be chemically or adhesively bonded to the rotatable sheath, fused, welded or otherwise engaged to the rotatable sheath.

In at least one embodiment the rotatable sheath is has a uniform material construction but is provided with sections of differing stiffness and/or flexural modulus by having the wall of the sheath be of varied thickness: providing one or more section of wall with a braided structure, while providing others with different braid or non-braided configurations; providing sections with one or multi-layer construction, pre-stretching one or more layers; selectively ablating or otherwise removing material from one or more layers; etc. In at least one embodiment, the sheath comprises end portions which have a greater thickness than the portion of the sheath therebetween about which the stent is mounted. In some embodiments the end portions abut the respective ends of the stent to minimize or prevent longitudinal displacement of the stent prior to delivery.

In at least one embodiment the sheath is comprised of a plurality of layers. In some embodiments an interior layer is comprised of one or more contact ribs which extend radially inward toward the balloon from a primary layer of the sheath. The rib may be a single inward protrusion defining a spiral, helical or other path about the balloon. The rib may be segmented to provide a plurality of spaced apart or segmented ribs.

In at least one embodiment the inner layer comprises a plurality of substantially circumferentially oriented ribs or annular rings. In some embodiments each rib may be a single continuous member extending substantially circumferentially about the interior of the primary layer. In some embodiments one or more of the ribs may be segmented and have one or more segments which are longitudinally offset from the segments circumferentially adjacent thereto.

In some embodiments the inner layer will be of a material having a higher durometer value than the primary layer. The higher durometer value and arrangement of the inner layer enables easier rotation of the sheath about the balloon by reducing the frictional interface between the balloon and sheath.

In at least one embodiment the sheath may be formed on a pin having one or more depressions into which an appropriate inner layer material such as thermo-set polymers, 2-part epoxies, UV curable polymers, etc. may be deposited. One the depressions are filled the pin may be over-coated with an appropriate primary layer material via injection molding, extrusion, spraying, dipping or other method.

In some embodiments the sheath may be provided with an external layer over the primary layer. The external layer may be of a softer durometer value than the primary layer to provide a contact layer for engagement of the stent in the reduced state.

In some embodiments the sheath may be configured to encourage a portion of the stent to have different deployment characteristics than the remainder of the stent. For example, in at least one embodiment a portion of the sheath may be provided with a region that is selectively thinned, removed, and/or other wise weakened. Such a "weakened" region on a selected portion of the sheath will allow a portion of the expanding balloon thereunder to push outward to a greater extent than those portion restricted by the rest of the sheath. As a result a weakened region may be positioned to allow a portion of the stent to be pushed into or against the ostium of branch vessel at a bifurcation. In some embodiments the weakened portion may be defined by a circumferential region of the sheath which is configured to be positioned under a central region of the stent. Such a configuration allows the sheath to encourage center-out deployment of the stent. Other deployment configurations may also be provided by varying the position of a weakened region of the sheath and/or by providing multiple regions.

These and other embodiments which characterize the invention are pointed out with particularity in the claims annexed hereto and forming a part hereof However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIG. 7a is a cross-sectional view of a portion of the sheath shown in FIG. 5a.

FIG. 8 is a longitudinal side view of a molding pin for use in the construction of the sheath shown in FIG. 5a.

DETAILED DESCRIPTION OF THE INVENTION

Figure 1:
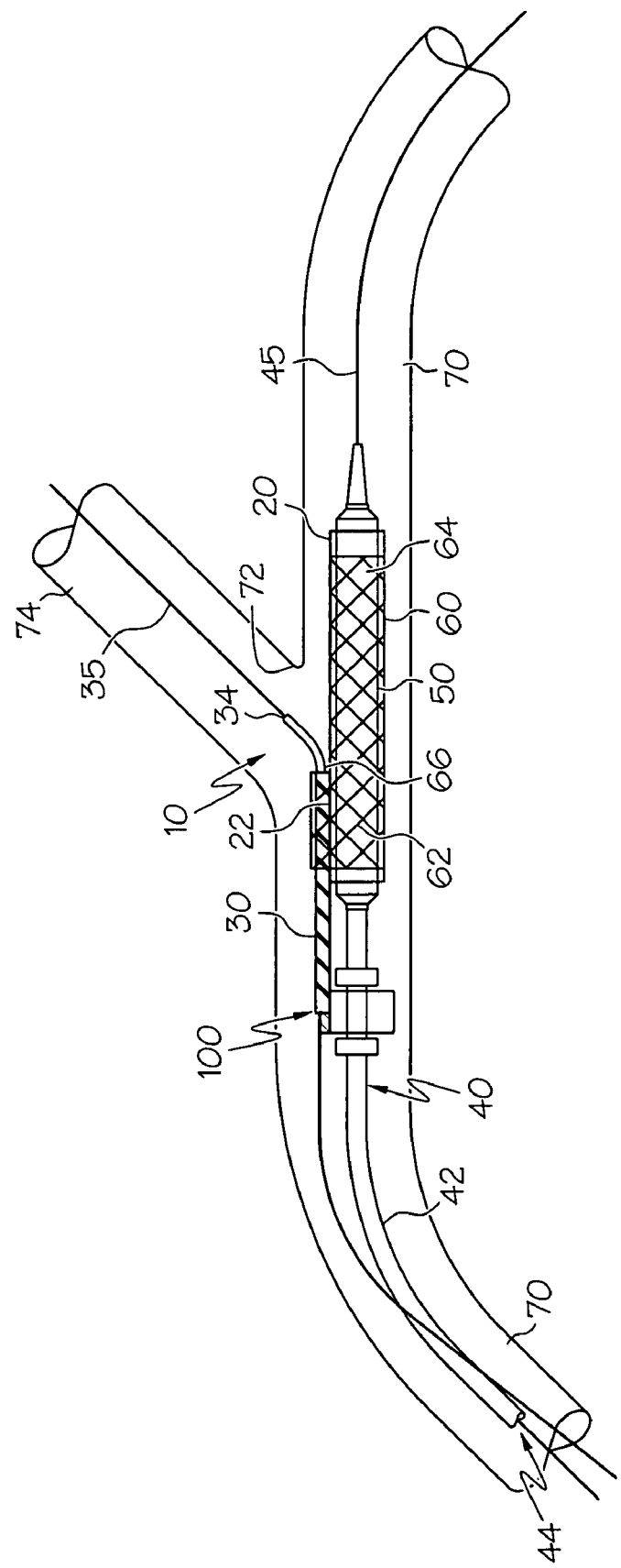
FIG. 1 is a longitudinal side view of an embodiment of the invention including a medical device shown being advanced to a vessel bifurcation

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, FIG. 1 illustrates a stent delivery system 100 having a rotatable sheath assembly 10 comprised of tubular sleeve or sheath 20 and a positioning or secondary guidewire housing 30. The assembly 10 is disposed about at least a portion of a balloon 50 of a catheter 40. The rotatable assembly 10 provides the system 100 with a rotating region that allows a stent 60 to be rotationally aligned within a primary vessel 70 so that a portion of the stent 60 is properly aligned at a bifurcation 72 of the vessel 70 and a branch vessel 74 such as in the manner depicted in FIG. 1.

Rotation of the assembly 10 may be imparted by a secondary guidewire 35 which passes through the a secondary guidewire lumen 34 defined by the secondary guidewire housing 30.

Figure 2:
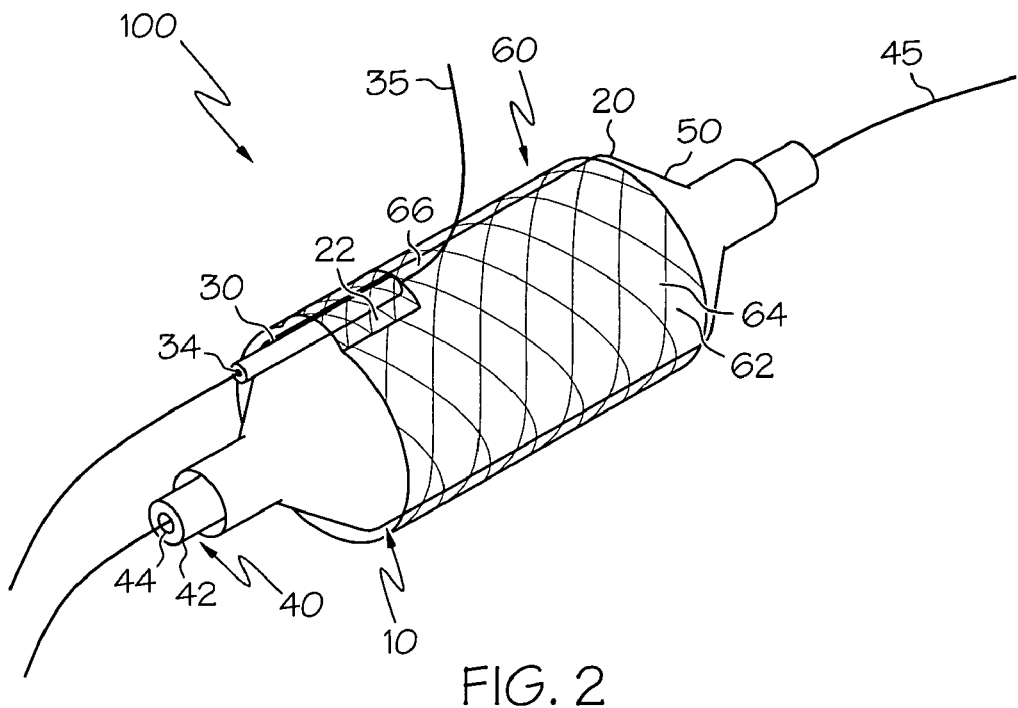
FIG. 2 is a partial perspective view of the medical device shown in FIG. 1
Figure 3:
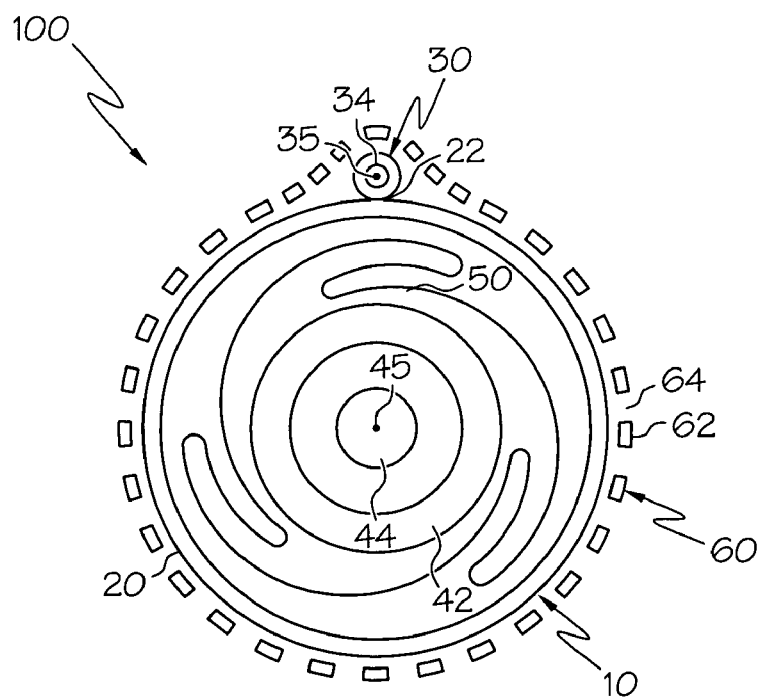
FIG. 3 is a cross-sectional view of a portion of the medical device shown in FIG. 2.

In at least one embodiment, such as in the example depicted in FIGS. 2-3, the housing 30 may be constructed of a wide variety of materials including metal plastic, etc. In some instances the housing 30 may be an external reinforcing member or hypotube. Such a hypotube may comprise stainless steel, nitinol, one or more polymer materials or other material. To improve flexibility, in some cases the housing 30 is provided with one or more openings, such as a slit, slot, etc. along its length. For example, the housing 30 may be spiral cut to provide a continuous opening which acts to provide improve the flexibility. In some embodiments the secondary guidewire housing 30 may comprise multiple layers and be comprised of a flexible inner shaft, about which a hypotube or other more rigid member may be disposed to protect the inner shaft and secondary guidewire 35. The flexible inner layer may be constructed of a variety of materials such as: PEBAX, nylon, urethane, and/or other materials in a single layer, multi-layer and/or braided configuration.

Examples of the rotating assembly 10 include a distal portion of the housing 30 being engaged to at least a proximal portion of the sheath 20 at an engagement site 22, such as is indicated in FIG. 3. The manner or mechanism of engagement between the sheath 20 and housing 30 may be by bonding, welding, adhering adhesively engaging, mechanically engaging or otherwise connecting the surfaces of the respective sheath 20 and housing 30.

In at least one embodiment the sheath 20 may be constructed by injection molding as a single piece.

In some embodiments, such as in the example depicted in FIGS. 1-3 the shaft 42 of the catheter 40 defines a primary guidewire lumen 44 through which a primary guidewire 45 may be advanced. In use, guidewires 35 and 45 are passed through a lumen or other body vessel 70 to a bifurcation 72, such as is shown in FIG. 1. Primary guidewire 45 continues along the primary or primary branch vessel 70 of the bifurcation 72 while the secondary guidewire 35 is advanced into the adjacent branch vessel 74 of the bifurcation 72. As the system 100 is advanced along both guidewires 35 and 45 simultaneously, as a result of the divergent paths defined by the guidewires 35 and 45, the rotatable sheath 20 will rotate as the position of the secondary guidewire 35 dictates thereby positioning the stent 60 into a desired position adjacent and/or within the branch vessel 74.

In some embodiments the stent 60 is comprised of a plurality of interconnected stent members 62 which define a plurality of openings 64. One of the openings may be characterized as a secondary opening 66 through which the secondary guidewire exits the housing 30 as well as from under the stent 60.

The sheath 20 is a hollow tube of sheath material that is configured to be placed over the balloon 50 or other region of a catheter 40, such as in the manner illustrated in FIGS. 1-3. The sheath 20 is further configured to be rotatable about the catheter shaft and/or balloon 50, even when a stent 60 has been positioned about and/or affixed to the sheath 20.

The sheath 20 may be constructed of a variety of materials and may include one or more layers of similar or dissimilar material(s). For example, in the embodiments depicted in FIGS. 5a-7c the sheath 20 comprises an outer layer 24 and an inner layer 26, wherein the inner layer 26 is at least partially constructed of a material having a higher durometer value than that of the material of the outer layer 24. As used herein "inner layer" refers to portion of the sheath 20 which is immediately adjacent to or in contact with the balloon 50 and/or catheter 40, whereas the term "outer layer" refers to the portion of the sheath 20 which is in contact with the stent 60 prior to deployment.

Figure 5A:
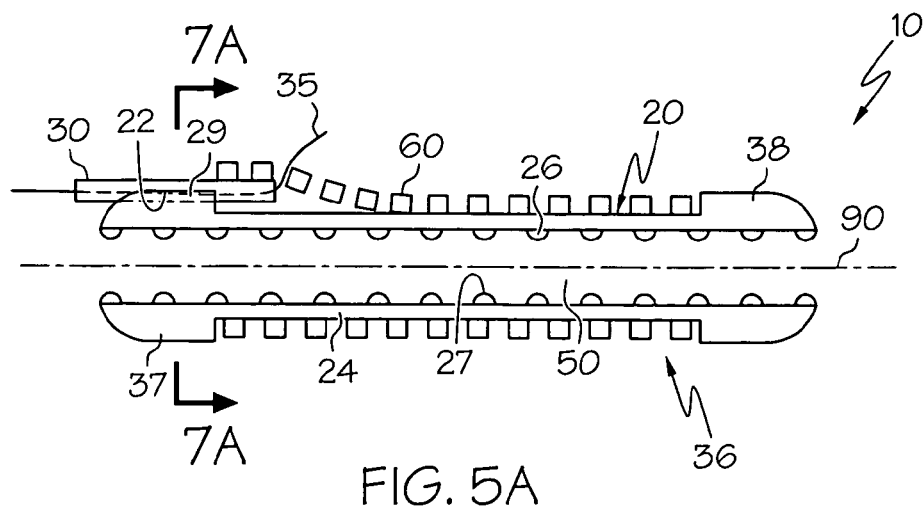
FIG. 5a is a longitudinal side view of a configuration of a rotatable sheath for use in the assembly depicted in FIG. 4.
Figure 5B:
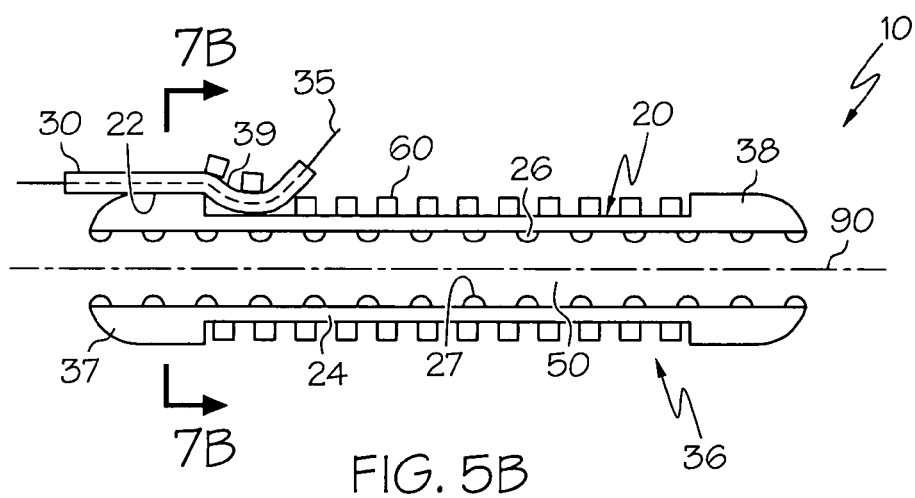
FIG. 5b is a longitudinal side view of a configuration of a rotatable sheath for use in the assembly depicted in FIG. 4.
Figure 5C:
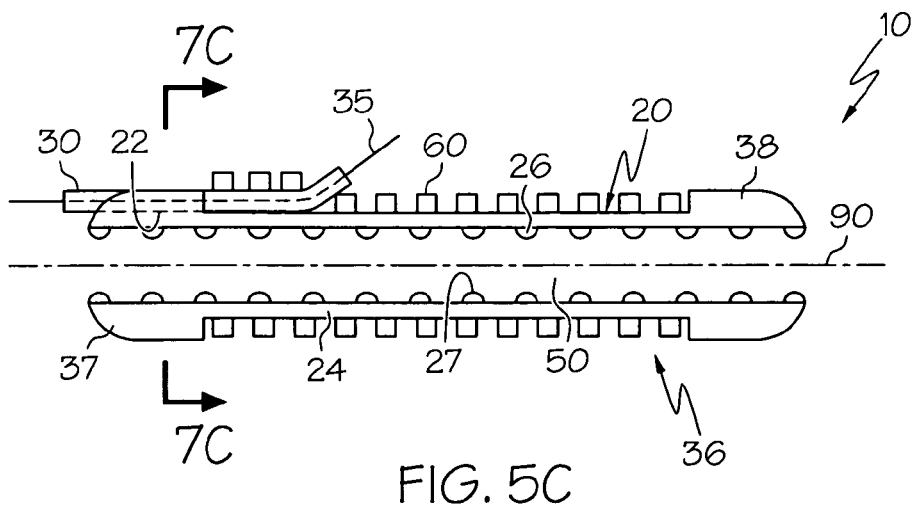
FIG. 5c is a longitudinal side view of a configuration of a rotatable sheath for use in the assembly depicted in FIG. 4.

As is shown in FIGS. 5a-5c and 6, the outer layer 24 defines a stent receiving region 36 upon which the stent 60 is positioned on the sheath prior to delivery. In some embodiments portions of the outer layer 24 adjacent to the stent receiving region 36 define two hubs or raised portions 37 and 38 which act to protect the stent from inadvertent longitudinal displacement during advancement of the system. As is shown in FIGS. 5a-5c, for the most part the hubs 37 and 38 have a thickness equal to or greater than the combined thickness of the stent receiving region 36 and the undelivered stent 60 positioned thereon. At the proximal end of the sheath 20 however, where the undelivered stent 60 overlays the secondary guidewire housing 30, a portion of the proximal end of the stent 60 may be radially external to the proximal hub 37. It is noted however that depending on the manner in which the secondary guidewire housing 30 is engaged to the sheath 20 the extent of any potential offset of the stent 60 relative to the proximal hub 37 will potentially vary.

Figure 4:
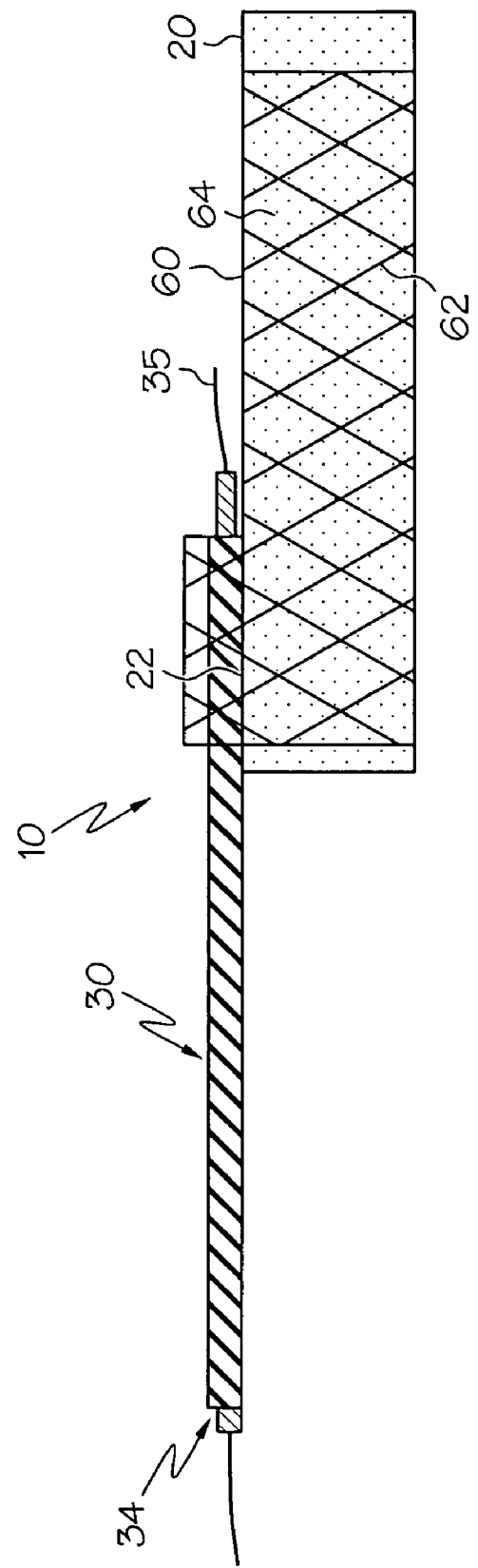
FIG. 4 is an enlarged longitudinal side view of the rotatable sheath assembly from the medical device shown in FIGS. 1-3.

In FIGS. 3 and 4 as well as in FIGS. 5a-5c (and in the corresponding cross-sectional views depicted in FIGS. 7a-7c) various configurations of the engagement region 22 between the secondary guidewire housing 30 and the sheath 20 are illustrated. In FIGS. 3 and 4 the secondary guidewire housing 30 is engaged directly to the external surface of the sheath 20. A weld or other engagement mechanism is utilized to engage the elements together along their common, substantially tangential interface. Other engagement configurations are certainly possible, such as by providing one or a plurality of engagement points along the interface rather than a single continuous engagement.

Figure 6:
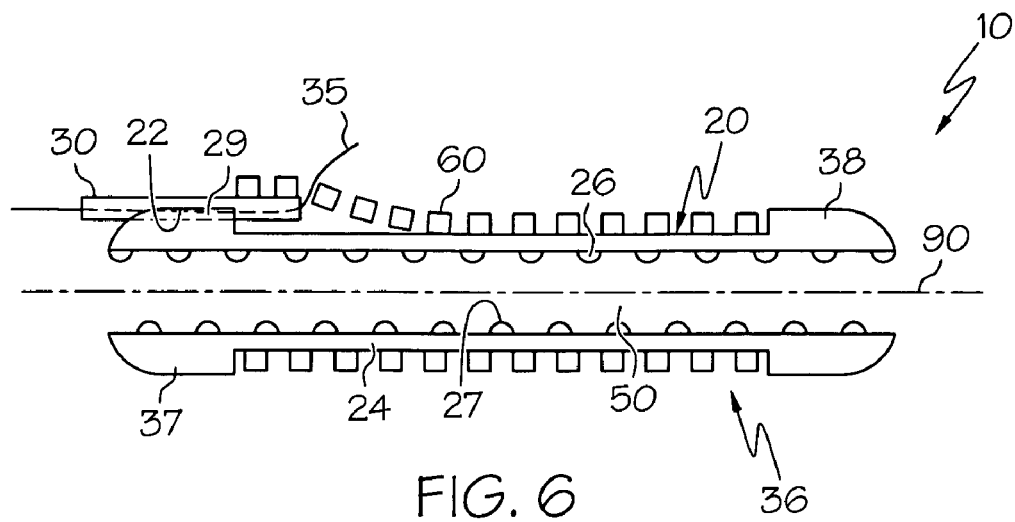
FIG. 6 is a longitudinal side view of a configuration of a rotatable sheath for use in the assembly depicted in FIG. 4.
Figure 7A:
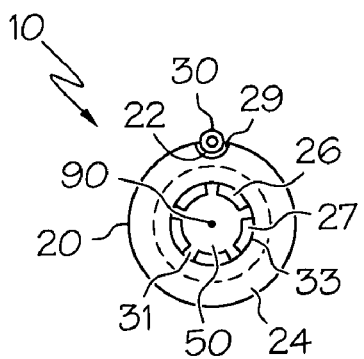

In another alternative, illustrated in FIGS. 5a, 6 and 7a, the sheath 20 is provided with a proximal recess or groove 29 into which at least a portion of the length of the housing 30 is positioned. In some embodiments the groove 29 has a depth sufficient to engage less than or more than about half of the circumferential surface of the portion of the housing 30 engaged thereto. In some embodiments, such as is shown in FIGS. 5c and 7c, the housing 30 is entirely surrounded by the sheath 20 thereby providing the assembly 10 with a minimum profile. In the configuration shown in FIGS. 5b and 7b the housing 30, rather than the sheath 20, has been modified to include a bent region 39 wherein the housing "descends" from the proximal hub 37 into the recess of the stent receiving region 36. Intuitively combinations of modifications to the sheath 20 and the housing 30 may be made to the assembly 10 in order to minimize profile, improve flexibility or otherwise alter the characteristics of the assembly and/or its components.

In the various figures of FIGS. 5a-7c, the multi-layer aspect of the sheath 20 is clearly illustrated. As indicated above, the inner layer 26 is positioned within the outer layer 24 and is constructed and arranged to rotatingly engage the balloon 50 during advancement of the system. To minimize the frictional engagement between the sheath 20 and the balloon 50 the relatively high durometer value inner layer 26 is embodied as one or more annular rings 27. Rings 27 provide the sheath 20 with a reduced contact area with the balloon 50 and thus aids in providing the system with improved rotation characteristics. Rings 27 may be provided in any pattern or configuration desired. For example, multiple rings may be uniformly spaced and circumferentially oriented relative to the balloon 50, such as in the embodiment depicted in FIG. 5a. As shown in FIG. 5a each of the rings 27 is substantially and uniformly perpendicular to a longitudinal axis 90 of the balloon 60. Alternatively, the rings may be slanted or angled relative to the longitudinal axis 90 balloon 60; they may be spaced in a random or non-uniform manner; they may be provided with differing thicknesses; etc. In at least one embodiment, such as is shown in FIG. 6, the inner layer 26 defines a single ring 27, which defines a spiral or a helical pattern about the balloon 50.

Regardless of the number and/or arrangement of the ring or rings 27, to further reduce the frictional interface between the balloon 50 and the sheath 20 a lubricant may be provided between the inner layer 26 and the balloon 50. Such a lubricant may be included as part of the inner layer 26 and/or the balloon 50. Alternatively, a lubricant is applied to the balloon 50 and/or the interior of the sheath 20 prior to assembly of the system.

Figure 7B:
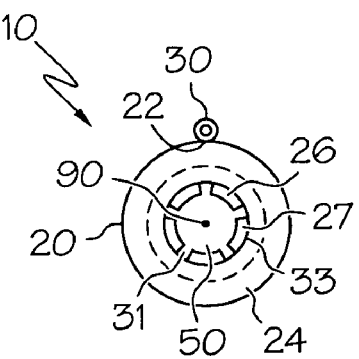
FIG. 7b is a cross-sectional view of a portion of the sheath shown in FIG. 5b.
Figure 7C:
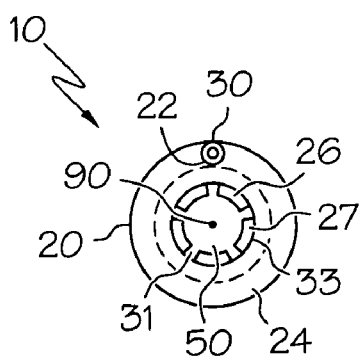
FIG. 7c is a cross-sectional view of a portion of the sheath shown in FIG. 5c.

In at least one embodiment, the contact surface between the balloon 50 and the sheath 20 may be further reduced by modifying the ring(s) 27 of the inner layer 26 to be segmented or discontinuous such as in the manner shown in FIGS. 7a-7c. A discontinuous ring 27 is provided with one or more spaces 31 between adjacent ring segments 33. Spaces and segments may have any shape or configuration desired, and preferably are configured to provide the assembly with improved rotation characteristics about the balloon 50.

Figure 8:
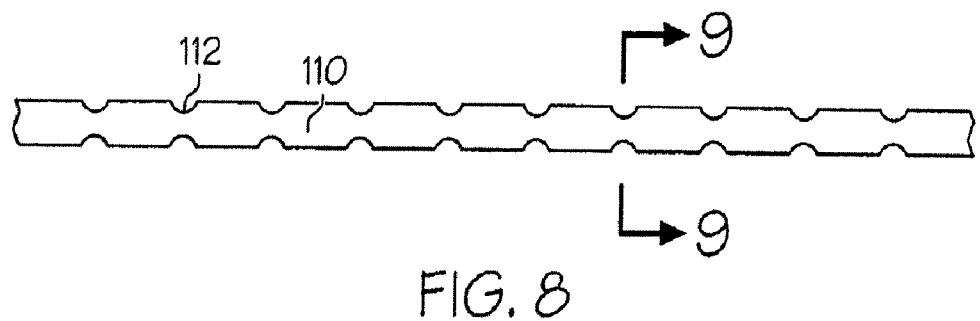

The unique multi-layer sheath 20 may be manufactured by a variety of methods. For example, a mandrel or pin 110 having a plurality of annular indentations 112, such as is depicted in FIG. 8 can be employed to manufacture the sheath 20 depicted in FIGS. 5a and 7a. In one manufacturing method, a material (or materials) suitable for use as the inner layer 26 of the sheath is deposited into the indentations 112. As previously mentioned the material of the inner layer 26 of the sheath will be of a harder durometer value than that of the outer layer material (or materials) and may include thermoset polymers, 2-part epoxies, UV curable polymers, and other materials as well.

Figure 10:
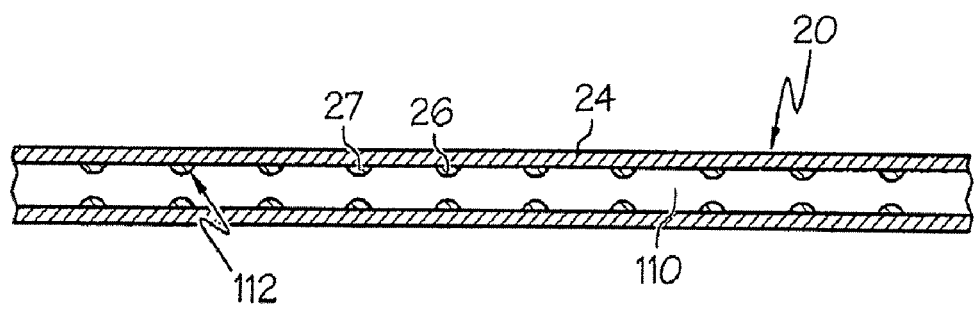
FIG. 10 is a longitudinal side view of the molding pin shown in FIGS. 8-9 with the sheath of the type shown in FIG. 5a being assembled thereon.

As depicted in FIG. 10, once the indentations 112 are filled, the pin 110 and inner layer 26 can be over-coated with the outer layer 24 material via injection molding, extrusion, spray coating, dip coating, etc. The resulting two-layer sheath 20 is removed from the pin 110.

In at least one embodiment the pin 110 may be constructed from Polyvinyl alcohol (PVA) or one or more similar materials. Where pin 110 is constructed of PVA the pin can be dissolved away following formation of the sheath 20 thereabout.

In at least one embodiment the indentations 112 are filled with a UV-curable resin, which is allowed to slightly cure. The pin 110 and inside layer 26 resin are then over-coated with the outside layer 24 material. A UV light source is applied to cure the resin and bond the layers 24 and 26 together. Once assembled a fluid such as air, etc may be injected along or through the pin 110 to partially expand the tube/sheath 20 to allow the sheath 20 to be removed from the pin 110.

Figure 9:
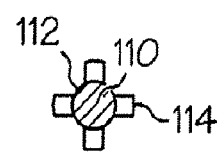
FIG. 9 is a cross-sectional view of a portion of the molding pin shown in FIG. 8.

To provide the inner layer 26 with segmented rings 27, in at least one embodiment, such as is shown in FIG. 9, the indentations 112 of the pin 110 may include one or more space forming members or protrusions 114 which are interspaced within the indentation and prevent a continuous ring from being formed.

Figure 11:
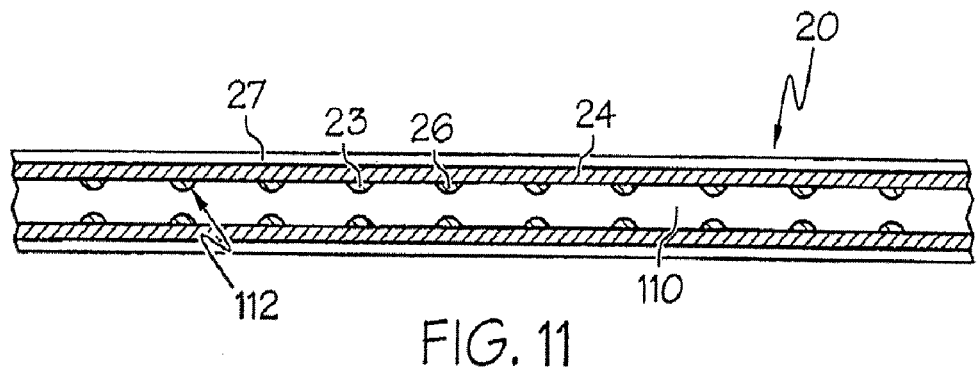
FIG. 11 is a longitudinal side view of the molding pin shown in FIGS. 8-9 with a configuration of a sheath being assembled thereon.

In some embodiments, it may be desirable to provide the sheath 20 with more than just an inner layer 26 and an outer layer 24. In at least one embodiment, such as in the example depicted in FIG. 11, one or more additional layers 23 may be applied to the sheath 20 by any mechanism desired. Additional layers may include one or more lubricious coatings, therapeutic agents, etc.

Turning now to the embodiments shown in FIGS. 12-15, as shown, the sheath 20 may be provided with one or more weakened, thinned, or otherwise modified regions 80, which allow the sheath 20 to provide some degree of control or limitation of the expansion characteristics of the balloon 50.

Figure 12:
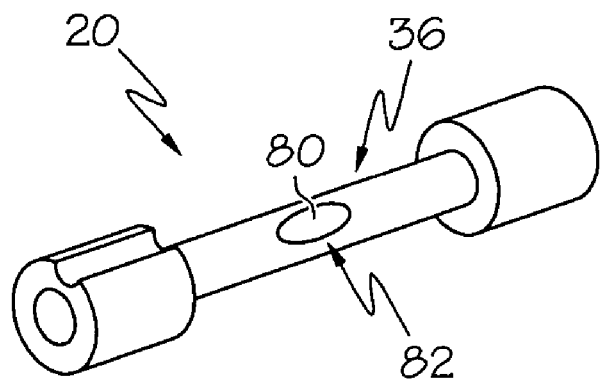
FIG. 12 is a perspective view of a configuration of a rotatable sheath for use in the assembly depicted in FIG. 4.
Figure 13:
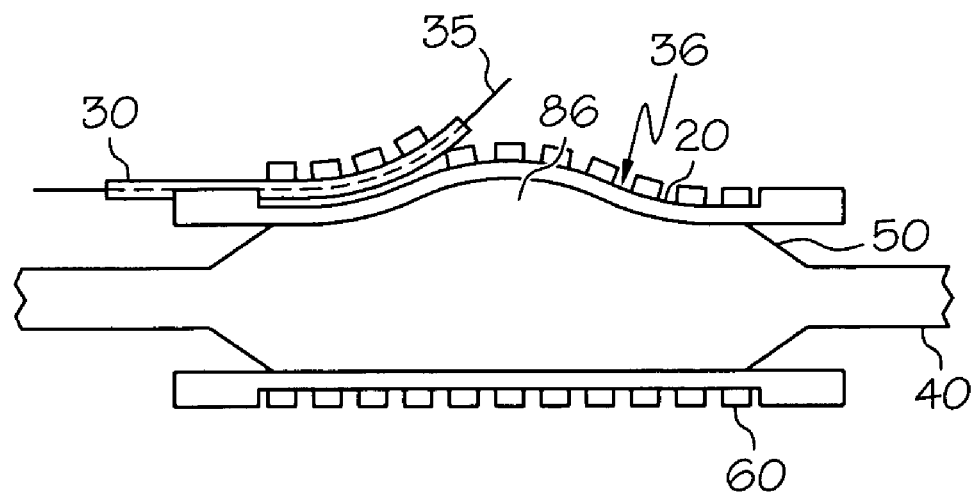
FIG. 13 is a longitudinal side view of the sheath shown in FIG. 12 depicted during balloon expansion and delivery of a stent.

In the embodiment depicted in FIGS. 12 and 13 for example, a middle portion 82 of the stent receiving region 36 of the sheath 20 is provided with a thinner area 80 than portions of the stent receiving region 36 adjacent thereto. As a result, the thinner area 80 of the sheath 20 will restrain the balloon 50 to a lesser extent than the rest of the sheath 20. As a result, when the balloon 50 is expanded the balloon 50 will push outward to a at and around the thinner area 80 before the rest of the balloon. This has the affect of allowing the balloon to form a "bulge" 86 which will tend to expand outward during expansion before areas of the balloon adjacent to the thinner area 80. Formation of such a bulge 86 is useful in pushing at least a portion of the stent 60 toward and even into a branch vessel of a bifurcation.

Figure 14:
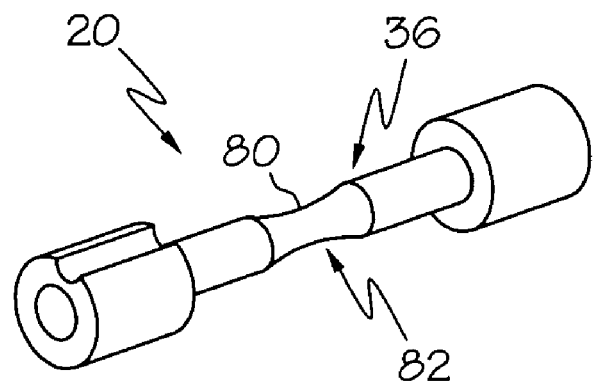
FIG. 14 is a perspective view of a configuration of a rotatable sheath for use in the assembly depicted in FIG. 4.
Figure 15:
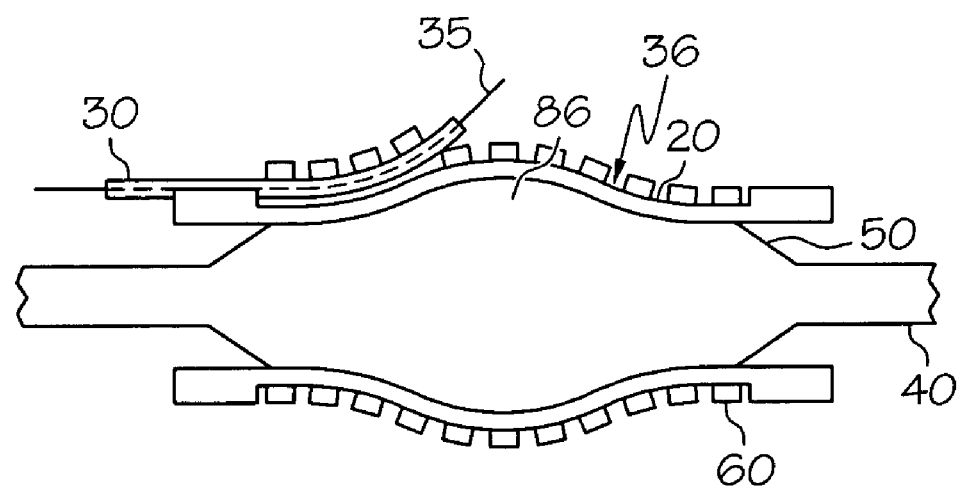
FIG. 15 is a cross-sectional longitudinal side view of the sheath shown in FIG. 14 depicted during balloon expansion and delivery of a stent.

Alternatively, by providing the sheath 20 with a thinner area 80 distributed about the circumference of the middle portion 82, such as is in the manner shown in FIGS. 14 and 15, the sheath 20 allows the balloon 50 to provide the stent 60 with a "center-out" (a.k.a. "center-up") deployment configuration. Center-out deployment of stents is often desired and is known and understood in the art.

Selectively thinning or otherwise modifying the sheath 20 in the manners described above may be accomplished by any of a variety of methods. For example, in at least one embodiment the sheath 20 may be selectively ablated by heat, laser ablation (photo-chemical process), mechanical, and/or chemical ablation, etc. to form the thinner area 80.

In the various embodiments discussed and/or illustrated herein, any portion of the system 100 and/or assembly 10 may be utilized to deliver one or more therapeutic agents or drugs to a delivery site such as within the vessel bifurcation or regions adjacent thereto.

To better accommodate placement of a therapeutic agent on the stent 60 in some instances one or more stent members may be configured to include one or more holes, notches, or other surface features to which one or more therapeutic agents may be placed for delivery to the aneurysm site. A therapeutic agent may be placed on the stent in the form of a coating. Often the coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic includes cellular material, the cellular material may include but is not limited to: cells of human origin and/or non-human origin as well as their respective components and/or derivatives thereof. Where the therapeutic agent includes a polymer agent, the agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device comprising:
a catheter, the catheter having a catheter shaft and a medical balloon positioned thereon, the balloon being expandable from an pre-expansion state to an expanded state;
a primary guidewire, wherein the catheter shaft defines a primary guidewire lumen for passage of the primary guidewire therethrough;
a secondary guidewire;
a rotatable assembly, the rotatable assembly comprising a sheath, the sheath being disposed about the balloon in both the pre-expansion state and in the expanded state, the sheath being rotatable about the balloon in the pre-expansion state, the sheath comprising an inner layer and an outer layer, the inner layer being in rotatable contact with the balloon, the outer layer being disposed about the inner layer, the inner layer being at least partially constructed of at least one material having a durometer value greater than that of the outer layer, wherein the sheath is longitudinally fixed relative to the balloon in the pre-expansion state; and
a secondary guidewire housing defining a lumen for passage of the secondary guidewire therethrough, wherein the secondary guidewire is moveable relative to the lumen of the secondary guidewire housing, at least a portion of the secondary guidewire housing being fixedly engaged to an exterior portion of the sheath.

2. The medical device of claim 1, further comprising a stent, the stent having a reduced diameter configuration and an expanded configuration, at least a portion of the outer layer of the sheath defining a stent receiving region, in the reduced diameter configuration the stent being disposed about the stent receiving region, at least a portion of the secondary guidewire passing between the sheath and at least a proximal portion of the stent.

3. The medical device of claim 2 wherein the at least a portion of the secondary guidewire is contained within the secondary guidewire housing.

4. The medical device of claim 3 wherein the inner layer of the sheath comprises at least one ring of the at least one material.

5. The medical device of claim 4 wherein the at least one ring defines a substantially spiral path about the balloon.

6. The medical device of claim 4 wherein the inner layer defines a plurality of adjacent, spaced-apart rings, each of the rings being substantially and uniformly perpendicular to a longitudinal axis of the balloon.

7. The medical device of claim 4 wherein the inner layer defines a plurality of adjacent, spaced-apart rings, each of the rings being substantially slanted relative to a longitudinal axis of the balloon.

8. The medical device of claim 4 wherein the at least one ring is segmented.

9. The medical device of claim 4 wherein the at least one ring comprises a plurality of spaced apart ring segments.

10. The medical device of claim 4 wherein the outer layer of the sheath comprises a pair of stent retaining hubs, each hub being positioned adjacent to an end of the stent receiving region, the stent receiving region and the stent in the reduced diameter configuration having a combined thickness no greater than that of the stent retaining hubs.

11. The medical device of claim 4 wherein the outer layer of the sheath defines a thickness, at least a portion of the outer layer defining a thinner region, the thickness of the thinner region being less than that of adjacent portions of the outer layer.

12. The medical device of claim 11 wherein when the balloon is expanded from the pre-expansion state to the expanded state a portion of the balloon underlying the thinner region will expand outward before regions of the balloon adjacent thereto.

13. The medical device of claim 1, wherein the sheath has a distal end and the secondary guidewire housing has a distal end, and the distal end of the secondary guidewire housing terminates at a location proximal of the distal end of the sheath.

14. The medical device of claim 13, wherein the secondary guidewire housing is fixedly engaged to an exterior portion of the sheath only at a proximal portion of the sheath.

15. The medical device of claim 14, wherein the secondary guidewire housing includes a proximal end and the sheath includes a proximal end, and the proximal end of the secondary guidewire housing is rotatably secured to the catheter shaft at a location proximal of the proximal end of the sheath.

16. The medical device of claim 15, wherein an axial position of the sheath and the secondary guidewire housing are fixed relative to an axial position of the balloon when the medical device is assembled.

17. The medical device of claim 1, wherein the sheath is formed as a separate piece from the secondary guidewire housing.

18. The medical device of claim 1, wherein an axial position of the sheath and the secondary guidewire housing are fixed relative to an axial position of the balloon when the medical device is assembled.

19. A medical device comprising:
a catheter shaft including a proximal region and a distal region, wherein the catheter shaft defines a primary guidewire lumen for passage of a primary guidewire therethrough;
a balloon disposed about a portion of the distal region of the catheter shaft, the balloon having a pre-expansion state and an expanded state;
a sheath disposed about at least a portion of the balloon, wherein the sheath is disposed about the balloon in both the pre-expansion state and in the expanded state, wherein the sheath is rotatable about the balloon when the balloon is in at least the pre-expansion state, wherein the sheath is axially secured relative to the balloon in at least the pre-expansion state;
a secondary guidewire housing including a proximal end, a distal end, and a lumen extending therebetween, the lumen configured for passage of a secondary guidewire therethrough, wherein the secondary guidewire is moveable relative to the lumen of the secondary guidewire housing, wherein at least a portion of the secondary guidewire housing is fixed relative to an outer surface of the sheath.

20. The medical device of claim 19, further comprising a stent including a proximal region and a distal region, wherein the proximal region of the stent is disposed about at least a portion of the sheath and at least a portion of the secondary guidewire housing, and wherein the distal region of the stent is only disposed about a portion of the sheath.

21. The medical device of claim 20 wherein the stent includes a side opening positioned intermediate the proximal region and the distal region, wherein the distal end of the secondary guidewire housing is aligned with the side opening of the stent.

22. The medical device of claim 19 wherein the sheath includes an inner layer and an outer layer, the inner layer being in rotatable contact with the balloon, the outer layer being disposed about the inner layer, the inner layer being at least partially constructed of at least one material having a durometer value greater than that of the outer layer.

23. The medical device of claim 19 further comprising:
a primary guidewire disposed in the primary guidewire lumen; and
a secondary guidewire disposed in the secondary guidewire lumen.

* * * * *